US010952677B2

(12) United States Patent
O'Dea

(10) Patent No.: US 10,952,677 B2
(45) Date of Patent: Mar. 23, 2021

(54) METHOD AND APPARATUS FOR RUPTURING AND DETECTING RUPTURING OF A MUSCLE, A MUSCLE FIBRE, A FIBRE MATERIAL OR A COATING IN OR ON A LUMEN, VESSEL OR SPHINCTER IN A HUMAN OR ANIMAL SUBJECT

(71) Applicant: Flip Technologies Limited, Galway (IE)

(72) Inventor: John O'Dea, Galway (IE)

(73) Assignee: FLIP TECHNOLOGIES LIMITED, Galway (IE)

( * ) Notice: Subject to any disclaimer, the term of this patent is extended or adjusted under 35 U.S.C. 154(b) by 294 days.

(21) Appl. No.: 15/575,625

(22) PCT Filed: May 20, 2016

(86) PCT No.: PCT/IE2016/000011
§ 371 (c)(1),
(2) Date: Nov. 20, 2017

(87) PCT Pub. No.: WO2016/185456
PCT Pub. Date: Nov. 24, 2016

(65) Prior Publication Data
US 2018/0153473 A1    Jun. 7, 2018

(30) Foreign Application Priority Data
May 21, 2015   (IE) .................................. S2015/0158

(51) Int. Cl.
*A61B 5/00* (2006.01)
*A61B 5/0538* (2021.01)
(Continued)

(52) U.S. Cl.
CPC ........ *A61B 5/6853* (2013.01); *A61B 5/02007* (2013.01); *A61B 5/0538* (2013.01);
(Continued)

(58) Field of Classification Search
CPC ............. A61B 5/6853; A61B 5/02007; A61B 5/0538; A61B 5/1076; A61B 5/4233; A61B 5/4519
(Continued)

(56) References Cited

U.S. PATENT DOCUMENTS

2010/0094328 A1*   4/2010   O'dea .................. A61B 5/0538
                                                                 606/192
2010/0113939 A1    5/2010   Mashimo et al.
(Continued)

FOREIGN PATENT DOCUMENTS

JP        05-056912 A      3/1993

OTHER PUBLICATIONS

Written Opinion of the International Searching Authority of PCT/IE2016/000011 dated Jul. 25, 2016.
(Continued)

*Primary Examiner* — Daniel L Cerioni
(74) *Attorney, Agent, or Firm* — Pearl Cohen Zedek Latzer Baratz LLP

(57) ABSTRACT

Apparatus for rupturing muscle fibres in a lower oesophageal sphincter comprises a balloon catheter. A multi-electrode impedance planimetry measuring system comprising a pair of stimulating electrodes and sensing electrodes is located on the catheter within the balloon for monitoring the diameter of the balloon when the balloon is inflated with a liquid saline solution from a reservoir through a flowmeter under the control of a microprocessor. The microprocessor computes the minimum diameter value from signals read from the sensing electrodes each time the cumulative volume of the liquid saline solution in the balloon increases by a predefined unit volume. The microprocessor computes a curve of a plot of the minimum diameter values against the corresponding cumulative volume values and determines the
(Continued)

Figure 1:
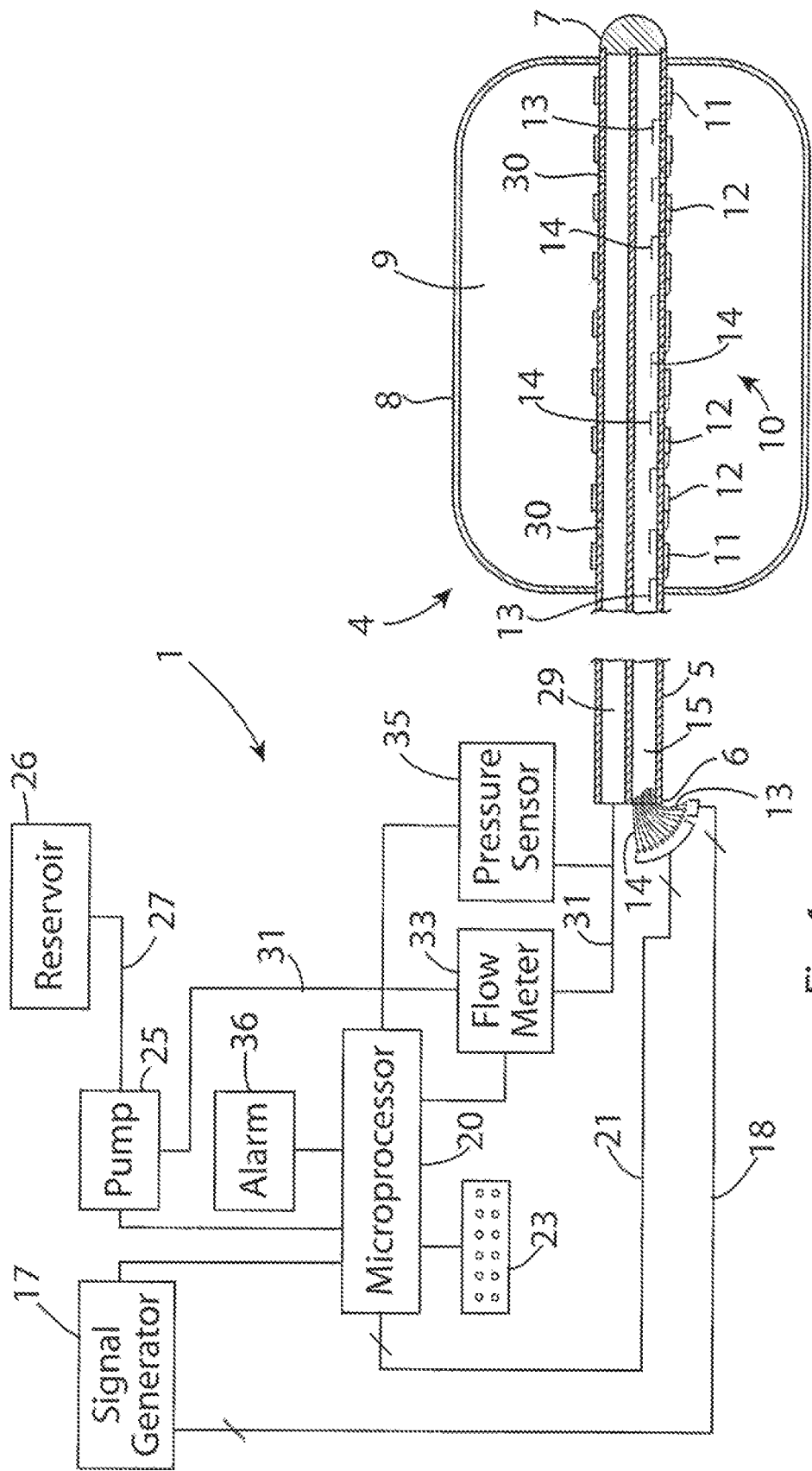

slope at each computed minimum diameter value. Rupture of the muscle fibres of the sphincter is determined at the point of inflection of the curve.

11 Claims, 3 Drawing Sheets

(51) Int. Cl.
    *A61B 5/107*      (2006.01)
    *A61B 5/02*      (2006.01)
    *A61B 5/03*      (2006.01)
    *A61B 5/0215*      (2006.01)
    *A61M 25/10*      (2013.01)

(52) U.S. Cl.
    CPC .......... *A61B 5/1076* (2013.01); *A61B 5/4233* (2013.01); *A61B 5/4519* (2013.01); *A61B 5/0215* (2013.01); *A61B 5/02021* (2013.01); *A61B 5/037* (2013.01); *A61M 2025/1022* (2013.01)

(58) Field of Classification Search
    USPC ........................................................ 600/587
    See application file for complete search history.

(56) References Cited

U.S. PATENT DOCUMENTS

| | | | |
|---|---|---|---|
| 2010/0228192 A1* | 9/2010 | O'Dea | A61B 5/1076 604/104 |
| 2010/0305479 A1* | 12/2010 | O'Dea | A61B 5/037 600/587 |
| 2010/0312181 A1* | 12/2010 | O'Dea | A61B 5/0538 604/96.01 |
| 2011/0054395 A1* | 3/2011 | O'Dea | A61B 5/1076 604/97.02 |
| 2012/0035642 A1 | 2/2012 | O'dea et al. | |
| 2015/0032031 A1* | 1/2015 | Hartwell | A61B 5/107 600/587 |

OTHER PUBLICATIONS

International Search Report of PCT/IE2016/000011 dated Jul. 25, 2016.

* cited by examiner

METHOD AND APPARATUS FOR RUPTURING AND DETECTING RUPTURING OF A MUSCLE, A MUSCLE FIBRE, A FIBRE MATERIAL OR A COATING IN OR ON A LUMEN, VESSEL OR SPHINCTER IN A HUMAN OR ANIMAL SUBJECT

CROSS REFERENCE TO RELATED APPLICATIONS

This application is a National Stage of International Application No. PCT/IE2016/000011 filed May 20, 2016, claiming priority based on Irish Patent Application No. S2015/0158 filed May 21, 2015, the contents of both of which are incorporated herein by reference in their entirety.

Apparatus (1) for rupturing muscle fibres in a lower oesophageal sphincter (2) comprises a balloon catheter (4) having a catheter (5) and a balloon (8) located at the distal end (7) of the catheter (5). A multi-electrode impedance planimetry measuring system (10) comprising a pair of stimulating electrodes (11) and sensing electrodes (12) is located on the catheter 5 within the balloon (8) for monitoring the diameter of the balloon (8) when the balloon (8) is inflated by a pump (25) with a liquid saline solution from a reservoir (26) through a flowmeter (33) under the control of a microprocessor (20). With the balloon (8) located in the sphincter (2) as the balloon (8) is being inflated, the microprocessor (8) computes the minimum diameter value of the balloon (8) from signals read from the sensing electrodes (12) each time the cumulative volume of the liquid saline solution in the balloon (8) increases by a predefined unit volume. The microprocessor computes a curve (40) of a plot of the minimum diameter values against the corresponding cumulative volume values of the liquid saline solution in the balloon (8) and determines the slope of the curve at each computed minimum diameter value. Rupture of the muscle fibres of the sphincter (2) is determined at the point of inflection (42) of the curve (40).

The present invention relates to a method and apparatus for rupturing and detecting rupturing of one of a muscle, muscle fibre, fibre material and a coating of a foreign material in a lumen, vessel or sphincter in a human or animal subject, for example, for rupturing and detecting rupturing of plaque in an artery, or a muscle or muscle fibre or calcification in a lumen, vessel or sphincter, for example, in the oesophagus or the lower oesophageal sphincter, although needless to say, the invention is not limited to a method and apparatus for rupturing and detecting rupturing of plaque in an artery or a muscle or muscle fibre in the oesophagus or in the lower oesophageal sphincter.

Within the oesophagus, in certain medical conditions, fibrous regions or rings cause narrowing which blocks the passage of food. These fibrotic regions, known as strictures can often arise due to radiation procedures. Such regions need to be dilated to open the oesophagus to a wider diameter to in turn ease the passage of food. In the lower oesophageal sphincter, the sphincter between the oesophagus and stomach, muscles serve to keep the sphincter shut when swallowing is not taking place. These muscles are activated by nerves signaling when swallowing is underway, causing the sphincter to open. However in a disorder, achalasia, there is impairment of the nerve action, leading to a situation where the sphincter remains shut. This is treated by rupturing the fibres during a dilation procedure, so as to allow food to passively pass through the now-disrupted sphincter.

Additionally, it is not unusual for arteries and other lumens or vessels in the cardiovascular system of a human or animal subject to become partly occluded with an internal coating of a relatively hard plaque material. Such occlusions can have serious consequences, and in general, it is desirable to open up such occlusions. Various techniques are known for opening such occlusions, for example, urging a boring tool and/or a reaming tool through the occlusion to bore through the occlusion and to open it. Other systems include use of a balloon catheter which is inflated in the occlusion in order to rupture the occlusion.

However, a problem with such balloon based systems is that it is impossible to identify precisely when the muscle, muscle fibre, plaque, calcification or other foreign material coating has been ruptured. In many cases dilation of the lumen, vessel or sphincter continues beyond the point where necessary. This leads to increased risk of rupturing of the lumen, vessel or sphincter. It is known that between 2% and 3% of oesophageal dilations lead to rupturing or perforation of the oesophagus, something which can have serious clinical consequences, in some cases leading to death of a subject.

There is therefore a need for a method and apparatus for rupturing and for detecting rupturing of a muscle, a muscle fibre, fibre material, a coating of a material, for example, plaque in or on a vessel, lumen or sphincter which addresses the problems of prior art apparatus.

The present invention is directed towards providing a method and an apparatus for rupturing and detecting rupturing of a muscle, muscle fibre, fibre material and a coating of a foreign material in or on a lumen, vessel or sphincter.

According to the invention there is provided apparatus for rupturing and detecting rupturing of one of a muscle, a muscle fibre, a fibre material and a coating of a foreign material in or on a lumen, vessel or sphincter in a human or animal subject, the apparatus comprising:

a balloon catheter comprising a balloon, the balloon being configured for locating in the lumen, vessel or sphincter adjacent the one of the muscle, muscle fibre, fibre material and the coating of a foreign material, a detecting means configured for locating in the balloon for detecting one of the diameter of the balloon, the transverse cross-section of the balloon, the rate of change of the diameter of the balloon and the rate of change of the transverse cross-section of the balloon, and for producing a signal indicative of the one of the diameter of the balloon, the transverse cross-section of the balloon, the rate of change of the diameter of the balloon and the rate of change of the transverse cross-section of the balloon, an inflating means configured for inflating the balloon with an inflating fluid, a monitoring means configured to monitor the signal produced by the detecting means for monitoring the one of the diameter of the balloon, the transverse cross-section of the balloon, the rate of change of the diameter of the balloon and the rate of change of the transverse cross-section of the balloon in response to each unit of inflating fluid delivered to the balloon during inflating thereof, and a determining means configured to determine rupturing of the one of the muscle, the muscle fibre, the fibre material and the coating of the foreign material in or on the lumen, vessel or sphincter in response to an increase in one of the diameter of the balloon,
the transverse cross-section of the balloon,
the rate of increase in the diameter of the balloon, and
the rate of increase in the transverse cross-section of the balloon, per unit of inflating fluid delivered to the balloon.

Preferably, a deactivating means is provided for deactivating the inflating means, the deactivating means being responsive to the determining means determining rupturing of the one of the muscle, the muscle fibre, the fibre material and the coating of the foreign material in or on the lumen, the vessel or sphincter.

Preferably, a measuring means is provided for measuring one of the volume and the flow rate at which the inflating fluid is being delivered to the balloon. Advantageously, the measuring means is configured to produce a signal indicative of one of the volume and the flow rate at which the inflating fluid is being delivered to the balloon. Ideally, the measuring means comprises a flowmeter.

In one aspect of the invention the detecting means comprises an impedance planimetry measuring system. Preferably, the detecting means comprises a multi-electrode impedance planimetry measuring system.

In another aspect of the invention the impedance planimetry measuring system comprises at least one stimulating electrode located on one of a catheter of the balloon catheter and the balloon thereof within the balloon, and at least one sensing electrode located on the one of the catheter and the balloon within the balloon and spaced apart from the stimulating electrode. Preferably, a pair of spaced apart stimulating electrodes are provided on the one of the catheter and the balloon within the balloon, and the sensing electrode is located on the one of the catheter and the balloon between and spaced apart from the stimulating electrodes. Advantageously, a plurality of spaced apart sensing electrodes are located on the one of the catheter and the balloon between and spaced apart from each of the stimulating electrodes. Ideally, each stimulating electrode and each sensing electrode is located on the catheter.

In one aspect of the invention the inflating fluid comprises an incompressible fluid. Preferably, the inflating fluid comprises an electrically conductive fluid.

In another aspect of the invention the monitoring and the determining means comprises a signal processor, and the signal processor is configured to read the signals from the detecting means and the measuring means.

In another aspect of the invention the signal processor is configured to compute the one of the diameter of the balloon, the transverse cross-section of the balloon, the rate of change of the diameter of the balloon and the rate of change of the transverse cross-section of the balloon from the signals read from the detecting means, during inflating of the balloon in response to each unit of the inflating fluid delivered to the balloon read from the signals from the measuring means.

Preferably, the signal processor is configured to determine rupture of the one of the muscle, the muscle fibre, the fibre material and the coating of the foreign material in or on the lumen, vessel or sphincter from the signals from the detecting means and the measuring means.

Advantageously, the signal processor is configured to determine rupture of the one of the muscle, the muscle fibre, the fibre material and the coating of the foreign material in or on the lumen, vessel or sphincter in response to detection of an inflection in a curve representative of the one of the diameter of the balloon, the transverse cross-section of the balloon, the rate of increase in the diameter of the balloon and the rate of increase in the transverse cross-section of the balloon, with respect to the one of the volume of the inflating fluid being delivered to the balloon and the rate of the inflating fluid being delivered to the balloon.

In one aspect of the invention the signal processor is configured to compute the one of the diameter of the balloon, the transverse cross-section of the balloon, the rate of increase in the diameter of the balloon and the rate of increase in the cross-section of the balloon adjacent the location in the balloon at which the cross-sectional area of the balloon is at its minimum value, with respect to the one of the volume of the inflating fluid being delivered to the balloon and the rate of delivery of the inflating fluid to the balloon. In another aspect of the invention the inflating means is operated under the control of the signal processor.

Preferably, the signal processor is configured to deactivate the inflating means in response to determining the rupture of the one of the muscle, the muscle fibre, the fibre material and the coating of the foreign material in or on the vessel, lumen or sphincter.

In another aspect of the invention a signal generator is provided for generating a stimulating signal and for applying the stimulating signal to one of the stimulating electrodes. Preferably, the signal generator is configured for applying the stimulating signal across the stimulating electrodes. Advantageously, the signal generator is operated under the control of the signal processor.

In another aspect of the invention the inflating means comprises a pump. Preferably, the pump is configured to pump the inflating fluid from an inflating fluid reservoir.

In another aspect of the invention a pressure sensing means is provided for monitoring a pressure indicative of the pressure of the inflating fluid in the balloon.

Preferably, the signal processor is responsive to signals read from the pressure sensing means for deactivating the inflating means in response to the pressure indicative of the inflating fluid in the balloon exceeding a predefined upper pressure.

In another aspect of the invention an input means is provided for inputting data to the signal processor.

Preferably, the signal processor comprises one of a microcontroller, a microprocessor, a computer, a laptop computer and a tablet computer.

In one aspect of the invention the apparatus is configured for rupturing and detecting rupturing of a coating of a foreign material on an inner surface of a lumen, vessel or sphincter.

In another aspect of the invention the apparatus is configured for rupturing and detecting rupturing of a coating of a foreign material surrounding an inner surface of a lumen, vessel or sphincter.

In a further aspect of the invention the apparatus is configured for rupturing and detecting rupturing of plaque in a lumen, vessel or sphincter.

In a still further aspect of the invention the apparatus is configured for rupturing and detecting rupturing plaque in an artery.

In another aspect of the invention the apparatus is configured for rupturing and detecting rupturing of a fibre material in or on a lumen, vessel or sphincter.

In another aspect of the invention the apparatus is configured for rupturing and detecting rupturing of a muscle or muscle fibre material surrounding a lumen.

In another aspect of the invention the apparatus is configured for rupturing and detecting rupturing of a muscle or muscle fibre material surrounding a vessel.

In a further aspect of the invention the apparatus is configured for rupturing and detecting rupturing of a muscle or muscle fibre material surrounding the sphincter.

The invention also provides a method for rupturing and detecting rupturing of one of a muscle, a muscle fibre, a fibre material and a coating of a foreign material in or on a lumen, vessel or sphincter in a human or animal subject, the method comprising:
- locating a balloon of a balloon catheter in the lumen, vessel or sphincter adjacent the one of the muscle, the muscle fibre, the fibre material and the coating of the foreign material to be ruptured,
- inflating the balloon with an inflating fluid,
- monitoring one of the diameter of the balloon, the transverse cross-section of the balloon, the rate of change of the diameter of the balloon and the rate of change of the transverse cross-section of the balloon in response to each unit of the inflating fluid delivered to the balloon during inflating thereof,
- determining rupture of the one of the muscle, the muscle fibre, the fibre material and the coating of the foreign material in response to an increase in one of
  - the diameter of the balloon,
  - the transverse cross-section of the balloon,
  - the rate of increase in the diameter of the balloon, and
  - the rate of increase in the transverse cross-section of the balloon, per unit of inflating fluid delivered to the balloon.

Preferably, inflating of the balloon with the inflating fluid is terminated in response to detection of rupturing of the one of the muscle, the muscle fibre, the fibre material and the coating of the foreign material in or on the lumen, vessel or sphincter.

In one aspect of the invention one of the volume of the inflating fluid being delivered to the balloon and the flow rate at which the inflating fluid is being delivered to the balloon is measured.

In another aspect of the invention one of the volume of the inflating fluid being delivered to the balloon and the flow rate at which the inflating fluid is being delivered to the balloon is measured by a flowmeter.

Preferably, the balloon is inflated with an incompressible fluid. Advantageously, the balloon is inflated with an electrically conductive fluid.

In one aspect of the invention the one of the diameter of the balloon, the transverse cross-section of the balloon, the rate of change of the diameter of the balloon and the rate of change of the transverse cross-section of the balloon is monitored from signals read from an impedance planimetry measuring system located within the balloon.

In another aspect of the invention the one of the diameter of the balloon, the transverse cross-section of the balloon, the rate of change of the diameter of the balloon and the rate of change of the transverse cross-section of the balloon is monitored from signals read from a multi-electrode impedance planimetry measuring system.

In another aspect of the invention the impedance planimetry measuring system comprises at least one stimulating electrode located on one of the catheter and the balloon within the balloon, and at least one sensing electrode located on the one of the catheter and the balloon, within the balloon and spaced apart from the at least one stimulating electrode. Preferably, a pair of spaced apart stimulating electrodes are provided on the one of the catheter and the balloon within the balloon, and the sensing electrode is located on the one of the catheter and the balloon between and spaced apart from the stimulating electrodes. Advantageously, a plurality of spaced apart sensing electrodes are provided on the one of the catheter and the balloon between and spaced apart from each of the stimulating electrodes. Ideally, each stimulating electrode and each sensing electrode is located on the catheter.

In another aspect of the invention rupture of the one of the muscle, the muscle fibre, the fibre material and the coating of the foreign material in or on the lumen, vessel or sphincter is determined in response to detection of an inflection in a curve representative of the one of the diameter of the balloon, the transverse cross-section of the balloon, the rate of increase in the diameter of the balloon and the rate of increase in the transverse cross-section of the balloon with respect to the one of the volume of the inflating fluid being delivered to the balloon and the rate of the inflating fluid being delivered to the balloon.

Preferably, rupture of the one of the muscle, the muscle fibre, the fibre material, and the coating of a foreign material in or on the lumen, vessel or sphincter is determined in response to detection of inflection in a curve representative of the one of the diameter of the balloon, the transverse cross-section of the balloon, the rate of increase in the diameter of the balloon and the rate of increase in the cross-section of the balloon adjacent the location in the balloon at which the cross-sectional area of the balloon is at its minimum value, with respect to the one of the volume of the inflating fluid being delivered to the balloon and the rate of delivery of the inflating fluid to the balloon.

In another aspect of the invention the one of the diameter of the balloon, the transverse cross-section of the balloon, the rate of change of the diameter of the balloon and the rate of change of the transverse cross-section of the balloon is computed during inflating of the balloon in response to each unit of the inflating fluid delivered to the balloon.

In another aspect of the invention a pressure of the inflating fluid indicative of the pressure of the inflating fluid in the balloon is measured.

Preferably, inflating of the balloon is terminated in response to the pressure indicative of the pressure of the inflating fluid in the balloon exceeding a predefined upper pressure.

In one aspect of the invention the method is configured for rupturing and detecting rupturing of a coating on an inner surface of a lumen, vessel or sphincter.

In another aspect of the invention the method is configured for rupturing and detecting rupturing of a coating of a foreign material surrounding an inner surface of a lumen, vessel or sphincter.

In a further aspect of the invention the method is configured for rupturing and detecting rupturing of plaque in a lumen, vessel or sphincter.

In a still further aspect of the invention the method is configured for rupturing plaque in an artery.

In another aspect of the invention the method is configured for rupturing a fibre material in or on a lumen, vessel or sphincter.

In a further aspect of the invention the method is configured for rupturing and detecting rupturing of a muscle or muscle fibre material surrounding a vessel.

In another aspect of the invention the method is configured for rupturing and detecting rupturing of a muscle or muscle fibre material surrounding a lumen.

In a further aspect of the invention the method is configured for rupturing and detecting rupturing of a muscle or muscle fibre material surrounding a sphincter.

The advantages of the invention are many. A particularly important advantage of the invention is that as well as rupturing the muscle, muscle fibre, fibre material, the coating of foreign material in or on a lumen, vessel or sphincter, the apparatus according to the invention also detects rupturing of the muscle, muscle fibre, fibre material or the coating of foreign material so that immediately upon detection of the rupturing of the muscle, muscle fibre, fibre material or coating of the foreign material, inflating of the balloon can be immediately terminated, thereby avoiding any possible danger to the lumen, vessel or sphincter. Additionally, by virtue of the fact that the apparatus according to the invention also detects the actual rupturing of the muscle, muscle fibre, fibre material or the coating of foreign material in or on the lumen, vessel or sphincter, there is no danger of failure to rupture the muscle, muscle fibre, fibre material or the coating of foreign material on the lumen, vessel or sphincter, or if rupturing of the muscle, muscle fibre, fibre material of the coating of the foreign material should fail to occur, the failure will be known since the method and apparatus will have failed to detect any rupturing.

A further advantage of the invention is achieved when a pressure sensing means is provided for monitoring the pressure of the inflating fluid in the balloon, in that by monitoring the pressure of the inflating fluid in the balloon, should the pressure increase to the maximum predefined pressure, inflating of the balloon immediately ceases, thereby avoiding any danger of the balloon bursting or rupturing the lumen, vessel or sphincter due to over-pressurising of the balloon.

Additionally, since the instant at which rupturing of the muscle, muscle fibre, fibre material or the coating of foreign material occurs is detected by the method and apparatus, only minimal dilation of the lumen, vessel or sphincter is required, and therefore, there is no risk of over dilation of the lumen, vessel or sphincter, which could otherwise lead to rupturing or perforation of the lumen, vessel or sphincter. Accordingly, the method and apparatus according to the invention minimises the clinical risks of procedures carried out using the method and apparatus according to the invention. This is a particularly important advantage when the method and apparatus is being used to rupture muscle fibres or other fibres in the lower oesophageal sphincter or in the oesophagus. However, it will be readily apparent to those skilled in the art that these advantages are also gained from the method and apparatus according to the invention when the method and apparatus are used for rupturing plaque, calcification or other foreign material coatings on a lumen vessel or a sphincter, for example, in an artery.

Figure 3:
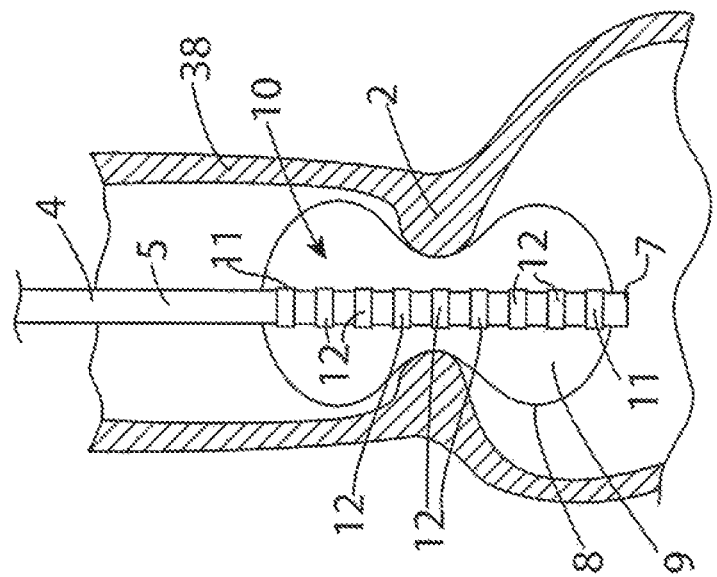
Figure 2:
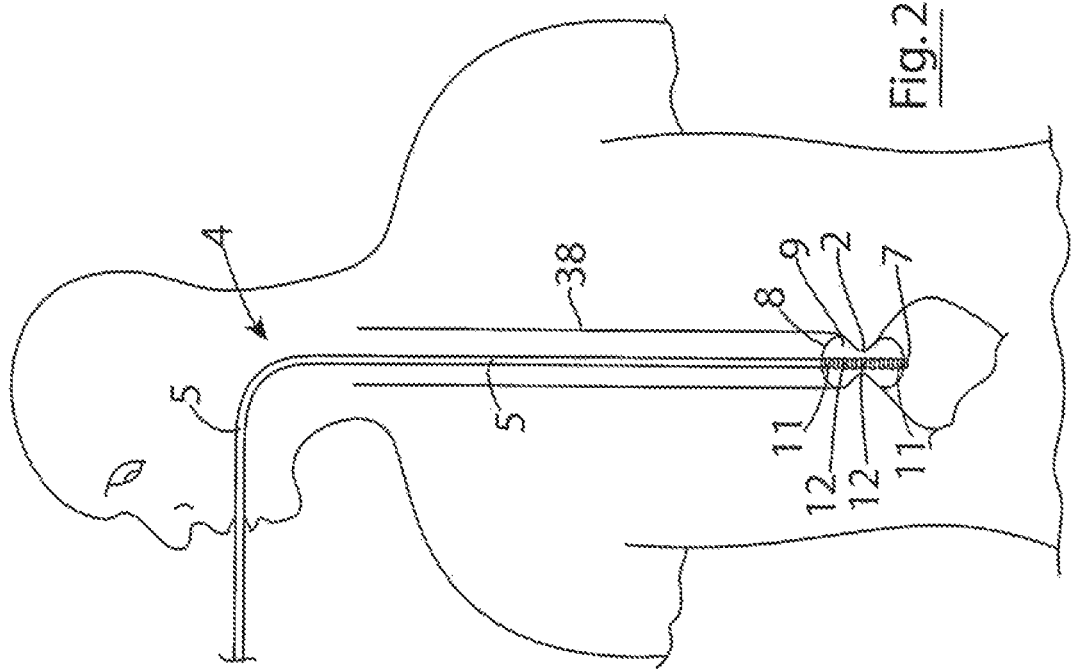
Figure 5:
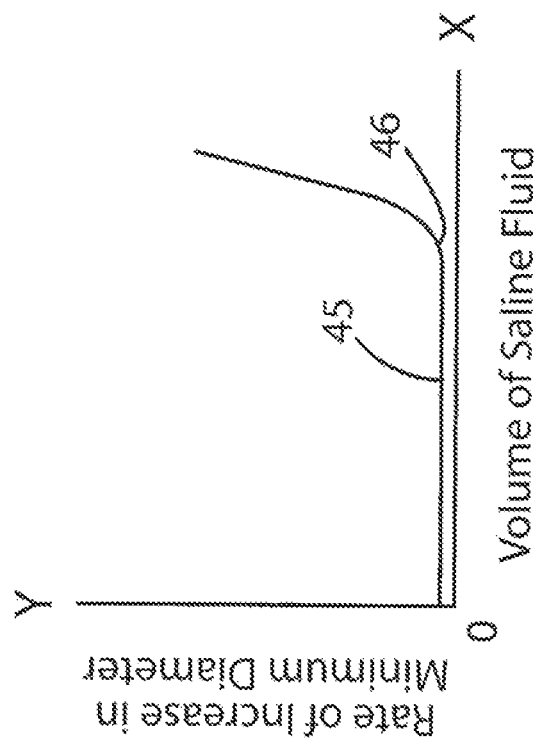
Figure 4:
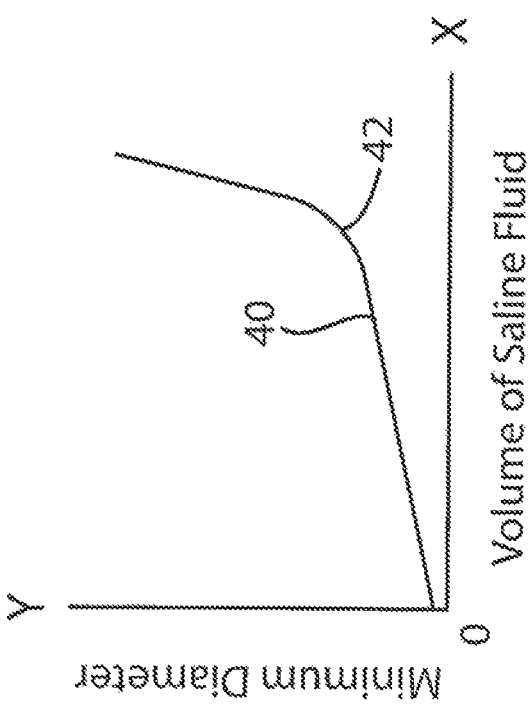

The invention will be more clearly understood from the following description of a preferred embodiment thereof, which is given by way of example only, with reference to the accompanying drawings, in which:

FIG. 1 illustrates a block representation of apparatus according to the invention for carrying out a method also according to the invention for rupturing and detecting rupturing of one of a muscle, muscle fibre, fibre material and a coating of a foreign material in or on a lumen, vessel or sphincter in a human or animal subject, FIG. 2 illustrates a representation of a portion of the apparatus of FIG. 1 in use in carrying out the method according to the invention for rupturing and detecting rupturing of muscle fibre surrounding a lower oesophageal sphincter in a human subject, FIG. 3 is an enlarged view of a detail of the portion of FIG. 2 of the apparatus of FIG. 1 also in use, FIG. 4 illustrates a graph of a plot of the diameter of a balloon of the apparatus of FIG. 1 plotted on the Y-axis against the volume of an inflating fluid in the balloon which is plotted on the X-axis, during inflating of the balloon in carrying out the method according to the invention, and FIG. 5 is a graph of a plot of the rate of increase of the diameter of a balloon of the apparatus of FIG. 1 plotted on the Y-axis against the volume of an inflating fluid in the balloon which is plotted on the X-axis, during inflating of the balloon in carrying out the method according to the invention.

Referring to the drawings and initially to FIGS. 1 to 3, there is illustrated apparatus according to the invention, indicated generally by the reference numeral 1, for carrying out a method also according to the invention for rupturing and detecting rupturing one of a muscle, muscle fibre, a fibre material and a coating of foreign material in or on a lumen, vessel or sphincter, in this case, for rupturing and detecting rupturing of muscle fibres which extend around the lower oesophageal sphincter 2 in a human subject. The apparatus 1 comprises a balloon catheter 4 comprising an elongated catheter 5 extending from a proximal end 6 to a distal end 7, and a balloon 8 located on the catheter 5 adjacent the distal end 7 thereof. The catheter 5 extends through the balloon 8 to define with the balloon 8 an annular hollow interior region 9 which extends around the catheter 5 within the balloon 8.

A detecting means comprising a multi-electrode impedance planimetry measuring system 10 is provided within the balloon 8 for monitoring the diameter or the transverse cross-sectional area of the balloon 8 at a plurality of locations longitudinally spaced apart along the catheter 5 as the balloon 8 is being inflated. In this embodiment of the invention the multi-electrode impedance planimetry measuring system 10 is configured for monitoring the diameter of the balloon 8. The multi-electrode impedance planimetry measuring system 10 comprises a pair of stimulating electrodes 11 provided by electrically conductive band electrodes extending around the catheter 5 and longitudinally spaced apart from each other along the catheter 5 within the balloon 8. A plurality of sensing electrodes 12 also provided by electrically conductive band electrodes extending around the catheter 5 are spaced apart from each other longitudinally along the catheter 5, and are located between the stimulating electrodes 11 and spaced apart longitudinally from the stimulating electrodes 11. In this embodiment of the invention the sensing electrodes 12 are equi-spaced apart from each other, and the spacing between the stimulating electrodes 11 and the adjacent one of the sensing electrodes 12 is similar to the spacing between the sensing electrodes 12, although it will be understood that the spacing between the stimulating electrodes 11 and the adjacent ones of the sensing electrodes 12 may be different to the spacing between the sensing electrodes 12, and it will also be appreciated that the sensing electrodes 12 need not necessarily be equi-spaced apart from each other, although in this embodiment of the invention they are equi-spaced apart.

Electrically conductive wires 13 extend from the stimulating electrodes 11 and electrically conductive wires 14 extend from the sensing electrodes 12 through a wire accommodating lumen 15 which extends through the catheter 5. The wire accommodating lumen 15 is closed at the distal end 7 of the catheter 5, and the wires 13 and 14 exit from the wire accommodating lumen 15 adjacent the proximal end 6 of the catheter 5.

A signal generator 17 is provided for applying an electrical stimulating signal, which may be a constant current or a constant voltage signal across the stimulating electrodes 11 for facilitating determining of the diameter of the balloon 8 as will be described below. The wires 13 from the stimulating electrodes 11 are connected to the signal generator 17, and a line 18 in FIG. 1 represents the wire connection of the wires 13 from the signal generator 17 to the stimulating electrodes 11.

A signal processor, in this embodiment of the invention a microprocessor 20 is programmed to control the operation of the apparatus 1. The signal generator 17 is operated under the control of the microprocessor 20 for applying the stimulating signals to the stimulating electrodes 11 as the balloon 8 is being inflated with an incompressible electrically conductive fluid, in this case a liquid saline solution, as will be described below. Signals from the sensing electrodes 12 are applied to the microprocessor 20 through the wires 14. The line 21 in FIG. 1 represents the connection of the wires 14 to the microprocessor 20. The microprocessor 20 is programmed to act as a monitoring means and is programmed to read the signals appearing on the sensing electrodes 12 in response to the stimulating signal applied to the stimulating electrodes 11 by the signal generator 17. The microprocessor 20 is programmed to act as a computing means and is programmed to compute the diameter values of the balloon 8 at locations corresponding to the locations of the sensing electrodes 12 on the catheter 5 from signals read from the sensing electrodes 12 in response to the stimulating signals applied to the stimulating electrodes 11 by the signal generator 17, as the balloon 8 is being inflated with the liquid saline solution. A keypad 23 is provided for inputting data manually into the microprocessor 20. However, any suitable input device instead of the keypad 23, for example a touchscreen, may be provided.

An inflating means, namely, a pump 25 operated under the control of the microprocessor 20 pumps the liquid saline solution from a reservoir 26 for inflating the balloon 8. An upstream conduit 27 connects the pump 25 to the reservoir 26. A fluid accommodating lumen 29 extends through the catheter 5 from the proximal end 6 thereof, and a plurality of communicating ports 30 extend from the fluid accommodating lumen 29 through the catheter 5 within the balloon 8 for communicating the fluid accommodating lumen 29 with the hollow interior region 9 of the balloon 8. The fluid accommodating lumen 29 is closed adjacent the distal end 7 of the catheter 5. A downstream conduit 31 extends from the pump 25 to the proximal end 6 of the catheter 5, and is connected to the fluid accommodating lumen 29 for communicating the pump 25 with the hollow interior region 19 of the balloon 8 for inflating thereof.

A measuring means, in this case, a flowmeter 33 is located in the downstream conduit 31 and monitors the volume of the liquid saline solution delivered by the pump 25 to the balloon 8. The microprocessor 20 is programmed to read signals from the flowmeter 33 and to compute the volume of the liquid saline solution being delivered to the balloon 8 during inflating of the balloon 8.

The microprocessor 20 is programmed to operate the pump 25 to inflate the balloon 8 with the liquid saline solution, and as the balloon 8 is being inflated to operate the signal generator 17 to apply the stimulating signal to the stimulating electrodes 11. The microprocessor 20 is programmed to read the signals appearing on the sensing electrodes 12 in response to the stimulating signal on the electrodes 11 and to compute the diameter values of the balloon 8 at the locations of the respective sensing electrodes 12, assuming that the balloon 8 when inflated is of circular transverse cross-section. The use of multi-electrode impedance planimetry measuring for determining either the diameter or the transverse cross-sectional area of a balloon when inflated with an electrically conductive fluid will be well known to those skilled in the art. The microprocessor 20 is programmed to compute the volume of the liquid saline solution delivered to the balloon 8 from the signals read from the flow meter 33 as the liquid saline solution is being delivered to the balloon 8 simultaneously as the diameter values of the balloon 8 are being computed.

A pressure sensing means, in this case a pressure sensor 35 is connected to the downstream conduit 31 and provides a signal which is indicative of the pressure of the liquid saline solution in the balloon 8. The microprocessor 20 is programmed to read signals from the pressure sensor 35, and to compute the pressure values of the liquid saline solution in the balloon 8 from the signals read from the pressure sensor 35 as the balloon 8 is being inflated. The microprocessor 20 is also programmed to compare the computed pressure values with a predefined maximum pressure value above which the pressure of the liquid saline solution in the balloon 8 should not exceed, and the microprocessor 20 is programmed to deactivate the pump 25 in the event of the computed pressure value exceeding the predefined maximum pressure value and to activate an audible alarm 36. The value of the predefined maximum pressure is inputtable into the microprocessor through the keypad 23.

In order to further describe the apparatus 1, its use in carrying out a method according to the invention for rupturing and detecting rupturing of the muscle fibres surrounding the sphincter 2 will now be described.

Initially the balloon catheter 4 is inserted into the oesophagus 38 either orally or nasally, and is urged downwardly through the oesophagus 38 until the balloon 8 is located and substantially centred end to end longitudinally in the sphincter 2, see FIGS. 2 and 3. On the balloon 8 being located in the sphincter 2, the microprocessor 20 operates the pump 25 to deliver the liquid saline solution from the reservoir 26 to the balloon 8 of the balloon catheter 4 for inflating the balloon 8. As the balloon 8 is being inflated, the balloon 8 will take up a waisted shape as illustrated in FIGS. 2 and 3, since the pressure of the muscle fibres of the sphincter 2 acting on the sphincter 2 to keep the sphincter 2 closed, results in the sphincter 2 bearing centrally on the balloon 8, which forces the balloon 8 to take up the waisted shape until the muscle fibres extending around the sphincter 2 have been ruptured.

The microprocessor 20 is programmed to read signals from the flowmeter 33, and at predefined time intervals of approximately 100 milliseconds to compute the cumulative volume of the inflating fluid delivered to the balloon 8 by the pump 25. The microprocessor 20 is programmed to operate the signal generator 17 to apply the stimulating signal across the stimulating electrodes 11 as the cumulative volume of the inflating fluid delivered to the balloon 8 increases by each predefined unit of volume of the liquid saline solution, and to simultaneously read the signals appearing on the sensing electrodes 12 in response to each stimulating signal. In this embodiment of the invention the value of the predefined unit of volume of the liquid saline solution is 0.5 ml, although it will be appreciated that the value of the predefined unit of the liquid saline solution may be greater or less than 0.5 ml. In general, the value of each predefined unit of volume of the liquid saline solution will be determined by the size of the balloon and the size of the lumen, vessel or sphincter, the muscle fibres of which or other fibre material or foreign coating thereof is to be ruptured. The microprocessor 20 is programmed to determine the diameter values of the balloon 8 at the locations of the respective sensing electrodes 12 from the signals read from the sensing electrodes 12 in response to the cumulative volume of the liquid saline solution delivered to the balloon 8 increasing by each predefined unit volume. The microprocessor 20 is further programmed to determine the minimum diameter value from each set of diameter values, which is effectively the minimum diameter value of the sphincter 2.

The microprocessor 20 is further programmed, that having determined the minimum diameter value of the balloon 8 which corresponds to each increase the cumulative volume of the liquid saline solution delivered to the balloon 8 by the predefined unit volume, to store the respective minimum diameter values of the balloon 8 cross-referenced with the corresponding value of the cumulative volume of the liquid saline solution delivered to the balloon 8. These minimum diameter values and the corresponding values of the cumulative volume of the liquid saline solution delivered to the balloon 8 are representative of a curve which would be indicative of a plot of the minimum diameter values against the corresponding cumulative volume values of the liquid saline solution delivered to the balloon 8.

In FIG. 4 a typical curve 40 of a graph of the minimum diameter values of the balloon 8 is plotted against the corresponding cumulative volume values of the liquid saline solution delivered to the balloon 8. The minimum diameter values of the balloon 8 are plotted on the vertical Y-axis, while the corresponding cumulative volume values of the liquid saline solution delivered to the balloon 8 are plotted on the X-axis.

The microprocessor 20 is programmed to compute the value of the slope of the curve 40 as each minimum diameter value of the balloon 8 is computed for each increase in the cumulative volume value of the liquid saline solution delivered to the balloon 8 by the predefined unit volume thereof. The microprocessor 20 is programmed to then compare the just computed value of the slope of the curve 40 with the previously computed values of the slope of the curve 40 for determining and detecting the point of inflection 42 of the curve 40.

As can be seen from the curve 40, the rate of increase in the minimum diameter value of the balloon 8 as the balloon 8 is being inflated remains substantially constant until the point of inflection 42 is reached. This part of the curve up to the point of inflection 42 is indicative of the sphincter 2 and the muscle fibres thereof being stretched. At the point of inflection 42, the rate of increase of the minimum diameter value of the balloon 8 with respect to the cumulative volume value of the liquid saline solution in the balloon 8 suddenly increases at a significantly greater rate than the rate of increase prior to the point of inflection 42, which is therefore indicative of the stretched muscle fibres of the sphincter 2 suddenly rupturing. The microprocessor 20 determines that rupturing of the muscle fibres of the sphincter 2 occurs when the slope of the curve 40 of the minimum diameter values with respect to the corresponding cumulative volume value of the liquid saline solution in the balloon 8 suddenly increases to be indicative of the point of inflection 42 of the curve 40. The microprocessor 20 is programmed at that stage to deactivate the pump 25 to prevent further inflating of the balloon 8 in the sphincter 2. The microprocessor 20 is programmed to operate the pump 25 in reverse to deflate the balloon 8 and to return the liquid saline solution from the balloon 8 to the reservoir 26, since the muscle fibres of the sphincter 2 have been ruptured. The balloon catheter 4 is then withdrawn from the subject.

Referring now to FIG. 5, an alternative method for determining and detecting rupturing of muscle fibre in a lower oesophageal sphincter similar to the lower oesophageal sphincter 2, using the apparatus 1 will now be described. In this embodiment of the invention the microprocessor 20 instead of being programmed to compute the values of a curve of a plot of the minimum diameter values against the cumulative volume values of the liquid saline solution delivered to the balloon 8, the microprocessor 20 is programmed to compute the values of the rate of increase of the diameter of the minimum diameter of the balloon 8 and to compute the values of a curve of a plot of the values of the rate of increase of the diameter of the minimum diameter of the balloon 8 plotted against the cumulative volume values of the liquid saline solution delivered to the balloon 8 as the cumulative volume of the liquid saline solution delivered to the balloon 8 increases by predefined unit of volume of the liquid saline solution. In this embodiment of the invention the value of the predefined unit volume of the liquid saline solution is also 0.5 ml.

In this embodiment of the invention after determining the minimum diameter value of the balloon 8 each time the cumulative volume of the liquid saline solution delivered to the balloon 8 increases by the predefined unit volume of the liquid saline solution, the microprocessor 20 is further programmed to compute the value of the rate of increase in the diameter of the minimum diameter of the balloon 8 each time the cumulative volume of the liquid saline solution delivered to the balloon 8 increases by the predefined unit volume of the liquid saline solution. The microprocessor 20 is programmed to store the computed values of the rate of increase in the diameter of the minimum diameter of the balloon 8 cross-referenced with the corresponding cumulative volume values of the liquid saline solution delivered to the balloon 8. These stored values are representative of a plot of the respective computed values of the rate of increase in the diameter of the minimum diameter of the balloon 8 against the corresponding cumulative volume values of the liquid saline solution delivered to the balloon 8.

FIG. 5 illustrates a curve 45 of a plot of the values of the rate of increase in the diameter of the minimum diameter of the balloon 8 against the corresponding cumulative volume values of the liquid saline solution delivered to the balloon 8. The values of the rate of increase in the diameter of the minimum diameter of the balloon 8 are plotted on the Y-axis, and the corresponding cumulative volume values of the liquid saline solution delivered to the balloon 8 are plotted on the X-axis.

The microprocessor 20 is programmed to compute the value of the slope of the curve 45 as the value of the rate of increase in the diameter of minimum diameter value of the balloon 8 is computed for each increase in the cumulative volume value of the liquid saline solution delivered to the balloon 8 by the predefined unit volume thereof. The microprocessor 20 is programmed to then compare the just computed value of the slope of the curve 45 with the previously computed values of the slope of the curve 45 for determining the point of inflection 46 of the curve 45.

As can be seen from the curve 45 of FIG. 5, the value rate of increase in the diameter of minimum diameter of the balloon 8 remains substantially constant until the value of the rate of increase in the diameter of the minimum diameter of the balloon 8 suddenly commences to significantly increase at the point of inflection 46 in the curve 45, which corresponds to rupturing of the muscle fibres in the sphincter 2. The part of the curve 45 up to the point of inflection 46 is indicative of stretching of the muscle fibres as the volume of the liquid saline solution delivered to the balloon 8 increases until the point of inflection 46 is reached, at which stage the significant increase in the value of the rate of increase in the diameter of the minimum diameter of the balloon 8 with respect to the cumulative volume value of the liquid saline solution delivered to the balloon 8 is thus indicative of rupturing of the muscle fibres of the sphincter 2.

On determining the point of inflection 46 of the curve 40 and determining rupturing of the muscle fibres of the sphincter 2 having ruptured, the microprocessor 20 deactivates the pump 25, and operates it in reverse to deflate the balloon 8 and to return the liquid saline solution from the balloon 8 to the reservoir 26. The balloon catheter 4 is then removed.

In both embodiments of the invention the microprocessor 20 of the apparatus 1 is programmed to read the signals produced by the pressure sensor 35 at predefined time intervals of approximately 100 milliseconds as the balloon 8 is being inflated with the liquid saline solution, and to compute the pressure of the liquid saline solution in the balloon 8 from the signals read from the pressure sensor 35. The microprocessor 20 is programmed to compare the computed pressure values with the predefined maximum pressure value. The microprocessor 20 is programmed so that in the event of the pressure of the saline solution in the balloon 8 reaching the predefined maximum pressure value, the microprocessor 20 deactivates the pump 25, and activates the alarm 36. The microprocessor 20 may also be programmed to reverse the operation of the pump 25 to fully or partially deflate the balloon 8 and return the liquid saline solution to the reservoir 26.

While the apparatus and the method have been described for rupturing and detecting rupturing of muscle fibres of a sphincter, it will be readily apparent to those skilled in the art that the apparatus and method may be used for rupturing and detecting rupturing of any muscle or other fibres of a sphincter, or any other lumen or vessel in a human or animal subject. For example, the apparatus and method according to the invention may be configured to rupture and detect rupturing of muscle or muscle fibre surrounding the oesophagus or any other such lumen or vessel.

Additionally, the apparatus and the method may be used for rupturing and detecting rupturing of a coating of a foreign material which typically could surround the inner surface of a vessel, lumen or sphincter, and in particular, plaque surrounding the inner surface of an artery or other blood vessel in a human or animal subject, and thus the apparatus and the method could also be configured for rupturing and detecting rupturing of plaque in an artery or other blood vessel or lumen in a human or animal subject. While the microprocessor has been described as being programmed to determine the diameter and the rate of increase of diameter in a balloon, it will be readily apparent that the microprocessor could be programmed to compute any other dimension or characteristic of the transverse cross-section of the balloon, for example, the transverse cross-sectional radius, circumference or area and/or the rate of change of the transverse cross-sectional radius, circumference or area from the signals read from the sensing electrodes 12 in response to the stimulating signal applied to the stimulating electrodes 11.

It is also envisaged that in certain cases, the balloon catheter may be provided with one single sensing electrode 12 located spaced apart from and between the stimulating electrodes 11, and in which case, the balloon would be located in the vessel, lumen or sphincter with the single sensing electrode aligned with the muscle, the muscle fibres, or other fibre material or the coating of the foreign material to be ruptured, so that the diameter values computed by the microprocessor from the signals read from the single sensing electrode would substantially correspond to the minimum diameter values of the balloon as the balloon is being inflated.

It is envisaged that the pump 25 may be dispensed with, and instead of the pump, a syringe with a graduated scale provided thereon may be provided for delivering the inflating fluid into the balloon. The graduated scale could be provided so that the volume of the inflating fluid delivered into the balloon could be read from the graduated scale. In which case, the flowmeter may also be dispensed with.

It is also envisaged that other inflating fluids besides a liquid saline solution may be used, and where a saline fluid is used, the saline fluid would in general be in liquid form. However, other inflating fluids could be used provided such inflating fluids had electrically conductive properties. While the inflating fluid has been described as being an incompressible fluid, which typically would be a liquid, it is envisaged in certain cases, that the inflating fluid may be a compressible fluid, such as, for example, a gas which would have electrically conductive characteristics.

It is also envisaged that a display means, for example, a visual display screen may be provided, and in which case, a visual representation of the balloon would be provided which would illustrate the transverse cross-section of the balloon, which could be illustrated in two-dimensional or three-dimensional form as the balloon is being inflated. It is also envisaged that the values of the diameters of the balloon adjacent the sensing electrodes could be displayed on the visual display screen at locations corresponding to the sensing electrodes on the catheter.

While in the description of the apparatus with reference to FIG. 4, the microprocessor has been described as being programmed to compute the slope values of the curve 40 of FIG. 4 of the plot of the minimum diameter values of the balloon against the cumulative volume values of the liquid saline solution delivered to the balloon, and to detect rupturing of the muscle fibres surrounding the lower oesophageal sphincter as being the point of inflection in the curve 40 of FIG. 4, it is envisaged that in cases where the liquid saline solution is delivered to the balloon at a constant flow rate, the microprocessor may be programmed to compute the slope values of a curve of a plot of the minimum diameter values of the balloon against time. In which case, the rupturing of the muscle fibres surrounding the lower oesophageal sphincter would be detected as having been ruptured at the point of inflection of the curve of the plot of the minimum diameter values of the balloon against time.

Additionally, while in the description of the microprocessor with reference to FIG. 5, the microprocessor has been described as being programmed to compute the slope values of the curve 45 of FIG. 5 of the rate of increase of the minimum diameter values of the balloon against the cumulative values of the liquid saline solution delivered to the balloon, and to detect rupturing of the muscle fibres surrounding the lower oesophageal sphincter as being the point of inflection in the curve 45 of FIG. 5, it is envisaged that in cases where the liquid saline solution is being delivered to the balloon at a constant flow rate, the microprocessor may be programmed to compute the slope values of a curve of a plot of the rate of increase of the minimum diameter values of the balloon against time. In which case, the rupturing of the muscle fibres surrounding the lower oesophageal sphincter would be detected as having been ruptured at the point of inflection of the curve of the plot of the rate of increase in the minimum diameter values of the balloon against time.

The invention claimed is:

1. Apparatus for rupturing and detecting rupturing of one of a muscle, a muscle fibre, a fibre material and a coating of a foreign material in or on a lumen, vessel or sphincter in a human or animal subject, the apparatus comprising:
a balloon catheter comprising a balloon, the balloon being configured for positioning in the lumen, vessel or sphincter adjacent the one of the muscle, muscle fibre, fibre material and the coating of a foreign material,
a plurality of sensors located in the balloon, the sensors configured for detecting one of the diameter of the balloon, the transverse cross-section of the balloon, the rate of change of the diameter of the balloon and the rate of change of the transverse cross-section of the balloon, and for producing a signal indicative of the one of the diameter of the balloon, the transverse cross-section of the balloon, the rate of change of the diameter of the balloon and the rate of change of the transverse cross-section of the balloon,
a fluid pump configured for inflating the balloon with an inflating fluid,
a processor configured to monitor the signal produced by the detecting means for monitoring the one of the diameter of the balloon, the transverse cross-section of the balloon, the rate of change of the diameter of the balloon and the rate of change of the transverse cross-section of the balloon in response to each unit of inflating fluid delivered to the balloon during inflating thereof, and
configured to determine rupturing of the one of the muscle, the muscle fibre, the fibre material and the coating of the foreign material in or on the lumen, vessel or sphincter in response to an inflection in a curve representative of an increase in one of
the diameter of the balloon,
the transverse cross-section of the balloon,
the rate of increase in the diameter of the balloon, and
the rate of increase in the transverse cross-section of the balloon, per unit of inflating fluid delivered to the balloon.

2. Apparatus as claimed in claim 1 in which the processor is provided for deactivating the fluid pump, the processor being responsive to the determined rupturing of the one of the muscle, the muscle fibre, the fibre material and the coating of the foreign material in or on the lumen, the vessel or sphincter.

3. Apparatus as claimed in claim 1 in which a flowmeter is provided for measuring one of the volume and the flow rate at which the inflating fluid is being delivered to the balloon, the flowmeter is configured to produce a signal indicative of one of the volume and the flow rate at which the inflating fluid is being delivered to the balloon.

4. Apparatus as claimed in claim 1 in which the plurality of sensors comprises an impedance planimetry measuring system, the plurality of sensors comprises a multi-electrode impedance planimetry measuring system.

5. Apparatus as claimed in claim 4 in which the impedance planimetry measuring system comprises at least one stimulating electrode located on one of a catheter of the balloon catheter and the balloon thereof within the balloon, and at least one sensing electrode located on the one of the catheter and the balloon within the balloon and spaced apart from the stimulating electrode, a pair of spaced apart stimulating electrodes are provided on the one of the catheter and the balloon within the balloon, and the sensing electrode is located on the one of the catheter and the balloon between and spaced apart from the stimulating electrodes, a plurality of spaced apart sensing electrodes are located on the one of the catheter and the balloon between and spaced apart from each of the stimulating electrodes, each stimulating electrode and each sensing electrode is located on the catheter.

6. Apparatus as claimed in claim 1 in which the inflating fluid comprises an incompressible fluid, the inflating fluid comprises an electrically conductive fluid.

7. Apparatus as claimed in claim 1 in which the processor comprises a signal processor, and the signal processor is configured to read the signals from the plurality of sensors and the flowmeter, the signal processor is configured to compute the one of the diameter of the balloon, the transverse cross-section of the balloon, the rate of change of the diameter of the balloon and the rate of change of the transverse cross-section of the balloon from the signals read from the plurality of sensors during inflating of the balloon in response to each unit of the inflating fluid delivered to the balloon read from the signals from the flowmeter, the signal processor is configured to determine rupture of the one of the muscle, the muscle fibre, the fibre material and the coating of the foreign material in or on the lumen, vessel or sphincter from the signals from the plurality of sensors, the signal processor is configured to determine rupture of the one of the muscle, the muscle fibre, the fibre material and the coating of the foreign material in or on the lumen, vessel or sphincter in response to detection of an inflection in a curve representative of the one of the diameter of the balloon, the transverse cross-section of the balloon, the rate of increase in the diameter of the balloon and the rate of increase in the transverse cross-section of the balloon, with respect to the one of the volume of the inflating fluid being delivered to the balloon and the rate of the inflating fluid being delivered to the balloon, the signal processor is configured to compute the one of the diameter of the balloon, the transverse cross-section of the balloon, the rate of increase in the diameter of the balloon and the rate of increase in the cross-section of the balloon adjacent the location in the balloon at which the cross-sectional area of the balloon is at its minimum value, with respect to the one of the volume of the inflating fluid being delivered to the balloon and the rate of delivery of the inflating fluid to the balloon.

8. Apparatus as claimed in claim 7 in which the fluid pump is operated under the control of the signal processor, the signal processor is configured to deactivate the fluid pump in response to determining the rupture of the one of the muscle, the muscle fibre, the fibre material and the coating of the foreign material in or on the vessel, lumen or sphincter.

9. Apparatus as claimed in claim 1 in which a signal generator is provided for generating a stimulating signal and for applying the stimulating signal to one of the stimulating electrodes, the signal generator is configured for applying the stimulating signal across the stimulating electrodes, operating under the control of the signal processor.

10. Apparatus as claimed in claim 1 in which the pump is configured to pump the inflating fluid from an inflating fluid reservoir, a pressure sensor is provided for monitoring a pressure indicative of the pressure of the inflating fluid in the balloon, and the signal processor is responsive to signals read from the pressure sensor for deactivating the fluid pump in response to the pressure indicative of the inflating fluid in the balloon exceeding a predefined upper pressure, and advantageously, an input means is provided for inputting data to the signal processor, and the signal processor comprises one of a microcontroller, a microprocessor, a computer, a laptop computer and a tablet computer.

11. Apparatus as claimed in claim 1 in which the apparatus is configured for rupturing and detecting rupturing of one of a coating of a foreign material on an inner surface of a lumen, vessel or sphincter, a coating of a foreign material surrounding an inner surface of a lumen, vessel or sphincter, plaque in a lumen, vessel or sphincter, plaque in an artery, a fibre material in or on a lumen, vessel or sphincter, a muscle or muscle fibre material surrounding a lumen, a muscle or muscle fibre material surrounding a vessel, and a muscle or muscle fibre material surrounding the sphincter.

* * * * *